United States Patent
Stasny et al.

(10) Patent No.: US 9,744,258 B2
(45) Date of Patent: *Aug. 29, 2017

(54) DIAPER LINING FOR TREATMENT OF DIAPER RASH

(71) Applicant: Bum Bum Diapers, LLC, Dallas, TX (US)

(72) Inventors: Cheryl Stasny, Dallas, TX (US); Melanie Youschak, Key West, FL (US); Carlos Richer, Garza Garcia Nuevo Leon (MX)

(73) Assignee: Bum Bum Diapers, LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/008,359

(22) Filed: Jan. 27, 2016

(65) Prior Publication Data
US 2016/0213528 A1 Jul. 28, 2016

Related U.S. Application Data

(63) Continuation-in-part of application No. 14/856,327, filed on Sep. 16, 2015, now Pat. No. 9,498,556.

(60) Provisional application No. 62/162,429, filed on May 15, 2015, provisional application No. 62/143,539, filed on Apr. 6, 2015, provisional application No. 62/108,418, filed on Jan. 27, 2015.

(51) Int. Cl.
| | |
|---|---|
| *A61K 8/02* | (2006.01) |
| *A61L 15/44* | (2006.01) |
| *A61L 15/40* | (2006.01) |
| *A61L 15/18* | (2006.01) |
| *A61F 13/511* | (2006.01) |
| *A61F 13/00* | (2006.01) |

(52) U.S. Cl.
CPC ........ *A61L 15/44* (2013.01); *A61F 13/00063* (2013.01); *A61F 13/51113* (2013.01); *A61K 8/0204* (2013.01); *A61L 15/18* (2013.01); *A61L 15/40* (2013.01); *A61L 2300/102* (2013.01); *A61L 2300/30* (2013.01)

(58) Field of Classification Search
CPC .................................................. A61K 8/0204
See application file for complete search history.

(56) References Cited

U.S. PATENT DOCUMENTS 7,771,735 B2   8/2010   Dvoracek et al.

*Primary Examiner* — Carlos Azpuru

(57) ABSTRACT

An embodiment of this disclosure provides a medical dressing. The medical dressing includes a first layer comprising a non-woven material capable of being liquid permeable. The medical dressing also includes a second layer comprising a topical composition and a solidifying agent. The second layer is positioned on a side of the first layer. The medical dressing also includes a third layer comprising a material capable of being liquid impermeable. The third layer is positioned on the second layer opposite the first layer.

17 Claims, 12 Drawing Sheets

DIAPER LINING FOR TREATMENT OF DIAPER RASH

CROSS-REFERENCE TO RELATED APPLICATIONS

This is a continuation-in-part application of application Ser. No. 14/856,327, filed Sep. 16, 2015, which claims the benefit of U.S. Provisional Application No. 62/108,418 entitled "DIAPER TO TREAT DIAPER RASH," filed on Jan. 27, 2015, U.S. Provisional Application No. 62/143,539 entitled "DIAPER TO TREAT DIAPER RASH," filed on Apr. 6, 2015, U.S. Provisional Application No. 62/162,429 entitled "DIAPER TO TREAT DIAPER RASH," filed on May 15, 2015. The content of the above-identified patent documents is incorporated herein by reference.

TECHNICAL FIELD

The present application relates generally to diaper liners and, more specifically, to a diaper liner for treatment of skin or diaper rash.

SUMMARY

For a more complete understanding of the present disclosure and its advantages, reference is now made to the following description taken in conjunction with the accompanying drawings, in which like reference numerals represent like parts:

An embodiment of this disclosure provides a medical dressing. The medical dressing includes a first layer comprising a non-woven material capable of being liquid permeable. The medical dressing also includes a second layer comprising a topical composition and a solidifying agent. The second layer is positioned on a side of the first layer. The medical dressing also includes a third layer comprising a material capable of being liquid impermeable. The third layer is positioned on the second layer opposite the first layer.

Various embodiments provide a medical dressing for treating diaper rash including and a top sheet comprising a non-woven material capable of being liquid permeable. The topical layer comprising 25% by weight of organic shea butter, 25% by weight of pure white beeswax, and a plurality of specialized ingredients.

Various embodiments provide a method for manufacturing a plurality of medical dressings. The method includes feeding a hydrophobic composition that is pressurized for use as a topical layer over a protective area for each of a plurality of medical dressings. The hydrophobic composition includes a topical composition mixed with a solidifying agent. The plurality of medical dressings is part of a spool sheet. The method includes applying the hydrophobic composition in a first pattern on at least a first portion of the spool sheet. The method includes applying the hydrophobic composition in a second pattern on at least a second portion of the spool sheet. The first pattern is differently positioned than the second pattern.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; and the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 8, discussed below, and the various embodiments used to describe the principles of the present disclosure in this patent document are by way of illustration only and should not be construed in any way to limit the scope of the disclosure. Although a baby is used as a reference throughout the disclosure, the diaper can be worn by any wearer that is dealing with skin rash, such as diaper rash, or any other related condition.

Irritant diaper dermatitis, more commonly known as diaper rash, occurs in infants and children, but can also affect people who are incontinent, paralyzed, or bedridden. Some causes of diaper rash include friction from the skin rubbing against the wet diaper, irritation from prolonged exposure to feces, urine, or other chemicals produced with the diaper, allergic reactions to materials produced or added to the diapers, and the like. Symptoms of diaper rash including red or irritated skin are easily identified on the skin in contact with diaper. Typical treatment of diaper rash includes cleaning, use of various creams, and air-drying the affected area, which sometimes requires leaving the diaper off for extended periods of time.

Many times when dealing with diaper rash there is not enough time for the normal recommended treatment of cleaning and allowing the affected area to dry, which is also not a very good option for babies who are not potty trained. Leaving the diaper rash untreated potentially leads to making the rash worse or increasing the likelihood of developing a level 2 diaper rash, including a yeast or other infections. Several approaches to address the issue include different treatment options, such as absorbent materials or a topical remedy, including creams and powders, for diaper rash. Absorbent materials are designed to remove as much wetness from the surface layer of the diaper in contact with the skin. The creams are designed to act as barriers, and the powders were designed to neutralize the pH of urine to reduce the acidity contact with the skin. These solutions add significant weight when being transported; increasing the challenge for a mom or health care specialist on the go, especially when diaper rash is not present and the solutions are not needed. One example embodiment is to take existing treatments of either powders or creams and incorporate them within the diaper or pad. However, creams create conditions prime for mold growth, and both powders and creams at times leak into the packaging, diaper bag, car seat, clothes, or basically anything with which the diaper comes into contact.

Figure 1:
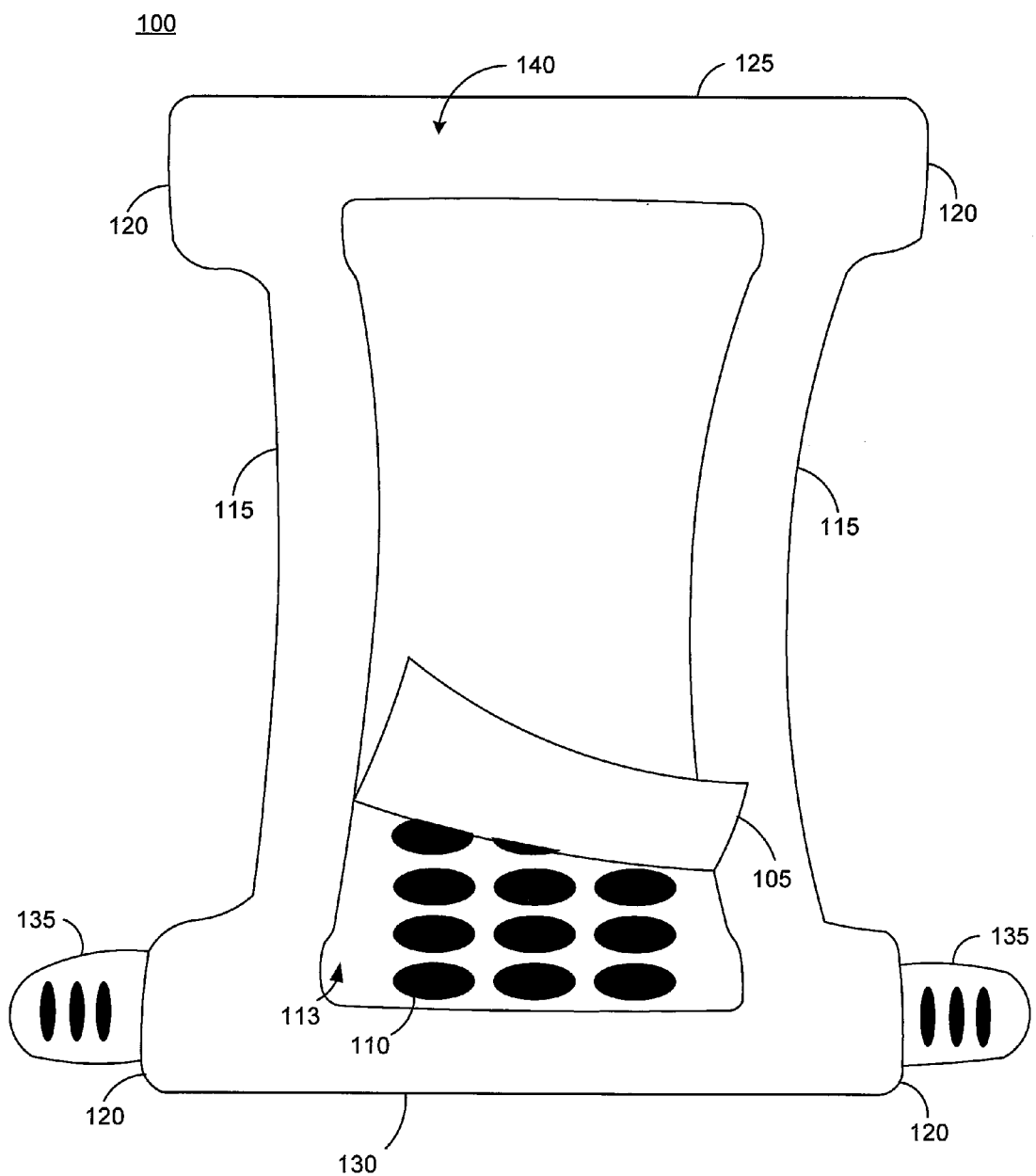
FIG. 1 illustrates a top view of a diaper with a portion of an enclosing layer separated from the diaper exposing the topical layer according to one embodiment of the present disclosure.

FIG. 1 illustrates a top view of a diaper 100 with a portion of an enclosing layer 105 separated from the diaper 100 exposing the topical layer 110 according to one embodiment of the present disclosure. The topical layer 110 can be defined as a composition, topical composition, permeable liner, or absorbent layer. The diaper 100 shown in FIG. 1 is for illustration only. Other embodiments could be used without departing from the scope of the present disclosure.

The diaper 100 is substantially rectangular in shape with the length concave for leg lining 115, located at center along both of the longer sides of the diaper 100, and four tabs 120, one located at each side of the front end 125 and the back end 130, meant for supporting and enclosing the diaper 100 around the wearer. The diaper 100 also includes two fasteners 135, one located on each of the tabs 125 on the back end 130, meant for securing the diaper 100 on the wearer. The fasteners 135 are for connecting to the tabs 120 located on the front end 125 of the diaper meant to hold the tabs 120 together around the wearer. The fasteners 135 are illustrated as sticky tabs, but can be any fastening method such as tape, clothespins, etc. The center of the diaper 100 contains a topical layer 110 covered by an enclosing layer 105. The enclosing layer 105 is comprised of a thin layer of light plastic-like material meant for enclosing and protecting the topical layer 110.

The topical layer 110 can also be referred to herein as a hydrophobic composition. The hydrophobic composition can be an anhydrous composition. In one example embodiment, the topical layer can include a topical composition and a solidifying agent. In one example embodiment, the solidifying agent can be a thin layer of wax or a wax-like substance. The wax or wax-like substance can be a dry wax that is capable of melting at a desired temperature. The topical composition can include various herbs, preservatives, emollients, and zinc oxide, or other ingredients or components. The solidifying agents solidify the composition so that the composition is a solid at room temperature. The solidifying agent may also improve the transfer by adhesion to the skin of the wearer.

Figure 2:
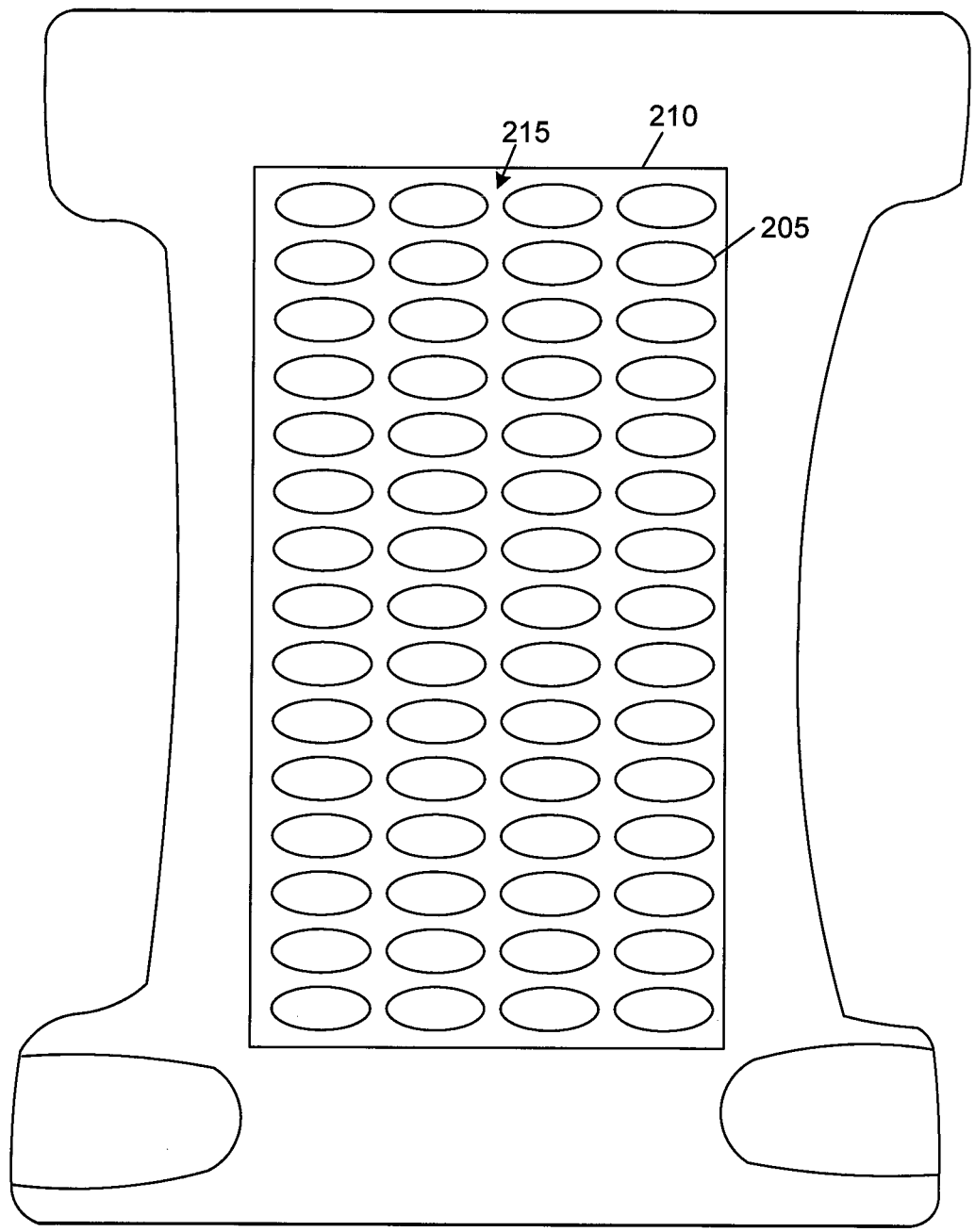
FIG. 2 illustrates an embodiment of the topical layer applied on an absorbent layer of a diaper in accordance with disclosed embodiments.
Figure 3:
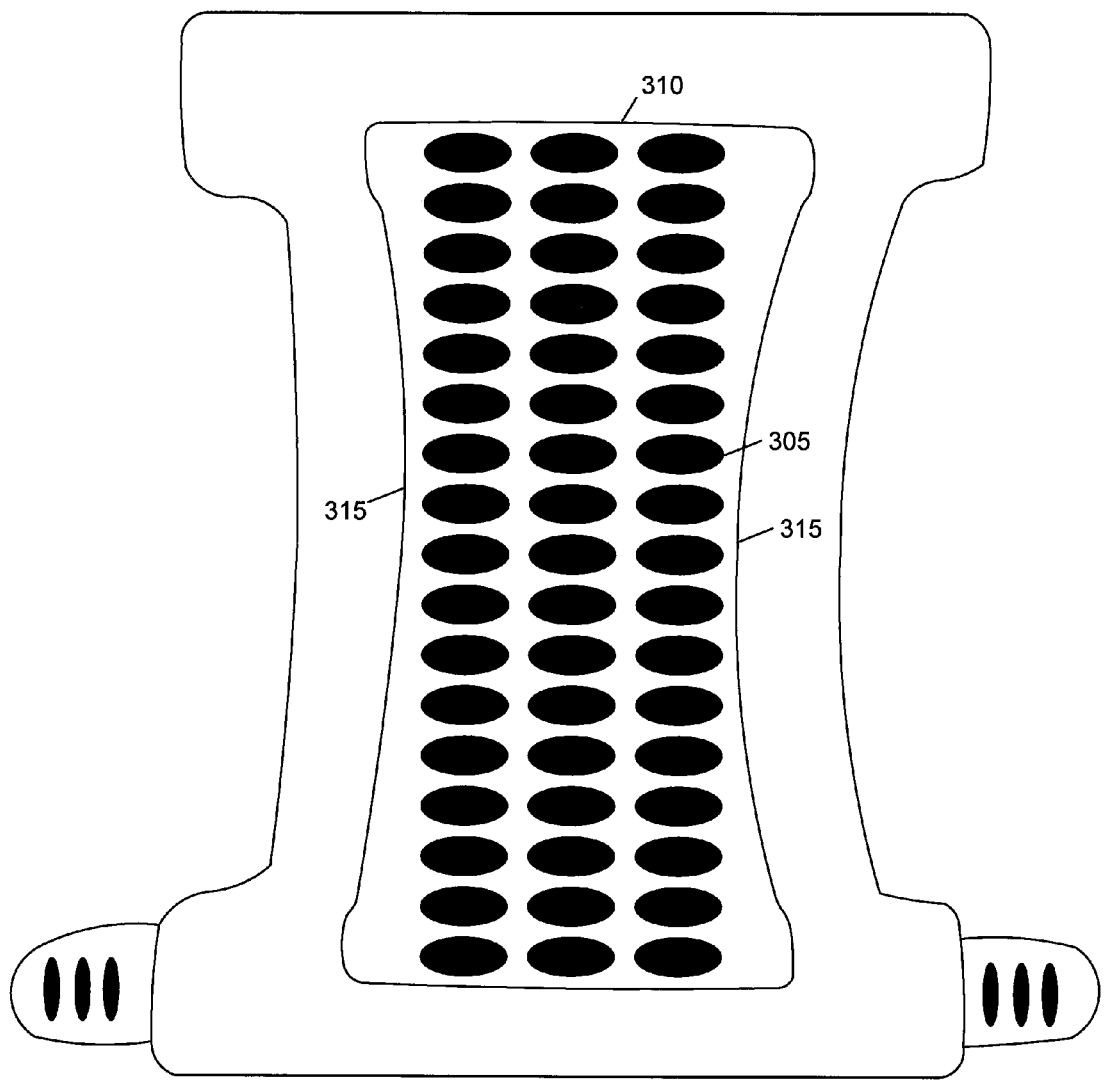
FIG. 3 illustrates an embodiment of the topical layer applied on an absorbent layer of a diaper in accordance with disclosed embodiments.

In one example embodiment, the topical layer 110 can cover a half or slightly more than half of the diaper 100 and can be structured in different shapes, as illustrated in FIGS. 2 and 3. The topical layer 110 is formed on the chassis 140 of the diaper 100, separate from any absorbent layers. The topical layer 110 can be formed on the top sheet 113 of the diaper 100. The top sheet 113 is the part of the diaper that comes in contact with the user's (baby or adult) skin. The top sheet 113 can be a hydrophilic non-woven material designed to quickly transfer fluids to the absorbent core of the diaper 100 while remaining soft and dry to the touch. The absorbent core typically consists of a blend of cellulose fluff pulp and polyacrylate granules. The cellulose portion quickly absorbs and transfers urine to the polyacrylate superabsorbent material, where it is trapped.

In certain embodiments, the topical layer 110 can be part of an insert, lining, or liner that can be attached or placed inside any type of diaper or pad. In this example embodiment, the topical layer 110 would not be on the top sheet 113, but instead would be part of an insert that could be applied to the diaper 100. In one example embodiment, the insert could be applied to the top sheet 113 by an adhesive layer of the insert. The insert could also include a top sheet to which the topical layer 110 is applied or positioned. The liner can also be a dressing, rash treatment dressing, dressing treated with rash wax to prevent and treat various skin conditions, and the like.

In one example embodiment, the topical layer 110 is meant to be a wax like substance and have a solid form at ambient temperature, but a low melting point or high viscosity. The topical layer 110 is meant to stay in solid form when the diaper 100 is not in use, but melts upon heating from the body temperature of the wearer due to the contact with the wearer and spreads on the wearer using friction of the body against the topical layer 110. Remaining in the wax form prevents the diapers 100 from creating an environment for mold to grow and reduces the possibility of leakage.

In different embodiments, the topical layer 110 can be formed in a solid layer, a patterned layer, a plurality of individual shapes, or distributed in any fashion. The distribution of the topical layer 110 is structured to optimize the location of the wax and also to provide flexibility for reduction of any material breaking off and causing a mess. The topical layer 110 can also be structured with a variable thickness. Furthermore, the amount of wax used is minimal compared to the weight of a cream or powder, allowing both greater comfort for the wearer of the diaper 100 and reduced hauling weight for the caregiver. The topical layer 110 also adds a minimal thickness to the diaper 100 to where the added thickness is negligible, which also increases the comfort for the wearer. The minimal thickness also allows the caregiver to pack more diapers 100 for longer outings, maintain a lighter weight of a diaper bag, or increases the amount of storage space.

In certain embodiments, the topical layer 110 is comprised of organic Shea butter and pure white beeswax. Along with those initial ingredients, the topical layer 110 includes specialized ingredients. In different example embodiments, for preventative care, the topical layer 110 can include 16%-40% zinc oxide powder, liquid lanolin (pure emollient oil), organic dandelion root powder, and chickweed herb powder. For sensitive skin, the topical layer 110 can include 16%-40% zinc oxide powder, liquid lanolin (pure emollient oil), organic aloe vera powder, and chamomile flowers. For corrective care, the topical layer 110 can include up to 40% zinc oxide powder, liquid lanolin (pure emollient oil), cod liver oil, and chamomile flowers powder. For overnight care, the topical layer 110 can include 16%-40% zinc oxide powder, organic lavender oil, and chamomile flowers powder.

In yet further embodiments, the topical layer 110 can include 40% zinc oxide powder, cod liver oil, chickweed herb powder, liquid lanolin, and dandelion root powder.

In one or more of the embodiments of this disclosure, the topical layer 110 can include:
25% by weight of Shea Butter;
25% by weight of pure white beeswax;
2% by weight of chickweed herb powder;
2% by weight of dandelion root powder;
40% by weight of zinc oxide powder;
4% by weight of cod liver oil; and
2% by weight of liquid lanolin.

The example topical layers can include other inactive or active ingredients. For example, the topical layer can include Theobroma cacao (cocoa) seed butter, which may be included in any amount, but in one example within 1%-25% by weight of the topical layer. The topical layer can include vegetable butter, which may be included in any amount, but in one example within 1%-10% by weight of the topical layer. The vegetable butter can be, for example, but not limited to, manoi butter, aloe butter, mango seed butter, cupuacu butter, and/or jojoba butter.

The topical layer can include caprylic/capric triglyceride, which may be included in any amount, but in one example within 1%-15% by weight of the topical layer. The topical layer can include cetyl esters, which may be included in any amount, but in one example within 1%-10% by weight of the topical layer. The topical layer can include lanolin, which may be included in any amount, but in one example within 0.5%-5% by weight of the topical layer. The topical layer can include lanolin oil, which may be included in any amount, but in one example within 0.5%-5% by weight of the topical layer.

The topical layer can include petrolatum, which may be included in any amount, but in one example within 1%-75% by weight of the topical layer. The topical layer can include mineral oil, which may be included in any amount, but in one example within 1%-10% by weight of the topical layer. The topical layer can include polyisobutene and/or hydrogenated polyisobutene, which may be included in any amount, but in one example within 1%-10% by weight of the topical layer. The topical layer can include squalene or squalene, which may be included in any amount, but in one example within 1%-10% by weight of the topical layer.

The topical layer can include dimethicone (silicone), which may be included in any amount, but in one example within 0.5%-10% by weight of the topical layer. The topical layer can include allantoin, which may be included in any amount, but in one example within 0.1%-0.5% by weight of the topical layer. The topical layer can include tocopheryl acetate (Vitamin E), which may be included in any amount, but in one example within 0.01%-1% by weight of the topical layer.

The topical layer can include natural oils, which may be included in any amount, but in one example within 0.5%-10% by weight of the topical layer. The natural oils can be, for example, but not limited to, coconut oil, soybean oil, olive oil, jojoba oil, borage oil, grape seed oil, sunflower seed oil, safflower oil, wheat germ oil, hydrogenated vegetable oil, rose hip oil, meadowfoam seed oil, macadamia seed oil, canola oil, chamomile oil, and/or lavender oil.

The topical layer can include stearyl alcohol, which may be included in any amount, but in one example within 0.5%-10% by weight of the topical layer. The topical layer can include stearic acid, which may be included in any amount, but in one example within 0.5%-10% by weight of the topical layer. The topical layer can include cetyl alcohol, which may be included in any amount, but in one example within 0.5%-10% by weight of the topical layer. The topical layer can include behenyl alcohol, which may be included in any amount, but in one example within 0.25%-5% by weight of the topical layer.

The topical layer can include solidifying agents, such as waxes and butters, which may be included in any amount, but in one example within 1%-10% by weight of the topical layer. The solidifying agents can be, for example, but not limited to, paraffin wax, microcrystalline wax, carnauba wax, candelilla wax, hydrogenated jojoba oil, rice bran wax, sunflower wax, siliconyl beeswax, polyethylene, synthetic wax, ceresin wax, ozokerite wax, other waxes, butters as described herein, as well as zinc oxide.

In one example embodiment, oils and butters derived from nuts (e.g., sesame oil, peanut oil, pistachio oil, etc.) can be used. In other embodiments, these oils may not be used.

In one or more embodiments, vegetable butters can be used within 1%-40% by weight of the topical layer.

In one embodiment, the topical composition includes monoi butter, which adds moisturizing benefits as well as essential aroma aspects to the finished product. Monoi butter can be made by steeping tiare flowers, a variety of gardenia indigenous to French Polynesia, in locally sourced coconut oil. The flowers contain high levels of methyl salicylate, known for its purifying and anti-inflammatory qualities.

In one embodiment, the topical composition includes aloe butter, which is an extract of aloe vera, aloe barbadensis, in a coconut fatty fraction. Aloe butter is semi solid at room temperature, but melts on the skin. Aloe Butter aids in rapid hydration of dry skin caused by eczema, psoriasis, rosacea, sun burn, wind burn, and general chapping.

In one embodiment, the topical composition includes mango seed butter, which provides relief for dry patches, flakiness, eczema and dermatitis flare-ups, and even psoriasis can benefit from daily application of mango butter, which goes to work deeply moisturizing and repairing damaged skin.

In one embodiment, the topical composition includes cupuacu seed butter, which due to high phytosterol levels has a naturally high water absorption capacity for long lasting moisture retention, providing relief for dry skin and hair. Cupuacu seed butter is also rich in antioxidants, including flavanoids, vitamins C, A, and B, five types of essential fatty acids, amino acids and minerals such as calcium and selenium. Applied topically, cupuacu seed butter soothes dry skin, is non-irritating, quickly absorbed.

In one embodiment, the topical composition includes jojoba butter, which absorbs very easily and does not feel greasy. Jojoba butter includes therapeutic properties for dry skin and eczema.

In one embodiment, the topical composition includes theobroma cacao seed butter, which temporarily protects injured or exposed skin from harmful or annoying stimuli and may provide relief to the skin. Theobroma cacao (cocoa) seed butter also slows the loss of water from the skin by forming a barrier on the skin's surface.

In one embodiment, the topical composition includes caprylic capric triglycerides, which are a specific fraction of coconut/palm oil fatty acids resulting in only the more stable, and skin loving, caprylic and capric fatty acids which creates a dry, silky oil form of esters. Caprylic capric triglycerides offer a noticeable silkiness in products, and exhibit excellent anti-oxidant properties to extend the natural shelf life. Caprylic capric triglycerides offer skin nurturing benefits due to the skin loving nature of the specific fatty acid esters, not seen with common fractionated coconut oil, or other carrier oils, and are especially suited to sensitive skin and oily skin.

In one embodiment, the topical composition includes cetyl esters, which can be a vegan alternative to beeswax. Cetyl Esters acts as a lubricant on the skin surface, providing a soft and smooth appearance.

In one or more embodiments, alternatives to oils can be used within 1%-10% by weight of the topical layer.

In one embodiment, the topical composition includes hydrogenated polyisobutene, which is synthetic oil that is used as a mineral oil substitute. Hydrogenated Polyisobutene is an emollient and moisturizer, and prevents water loss. Hydrogenated Polyisobutene allows for SPF retention even after water exposure (like in waterproof sunscreens).

In one embodiment, the topical composition includes squalane oil. Squalane is a natural lubricant and skin barrier that helps protect the skin and prevent moisture loss. Squalane also has a high penetration efficiency that makes it an excellent transport system that helps the skin absorb other ingredients.

In one embodiment, the topical composition includes allantoin oil, which is a natural soothing, anti-irritant, and skin protectant that increases the water content of the extracellular matrix which provides structural support to cells and is an important part of connective tissue. Allantoin also increases the smoothness of the skin; promotes cell replication; and promotes the healing of wounds, burns, and scars.

In one embodiment, the topical composition includes chamomile oil. The health benefits of camomile essential oil can be attributed to its properties as an antispasmodic, antiseptic, antibiotic, antidepressant, antineuralgic, antiphlogistic, carminative, cholagogue, cicatrisant, emenagogue, analgesic, febrifuge, hepatic, sedative, nervine, digestive, tonic, antispasmodic, bactericidal, sudorific, stomachic, anti-inflammatory, anti-infectious, vermifuge, and vulnerary substance. There are antiseptic and antibiotic properties which do not let biotic infections develop, which are those infections due to biotic factors such as bacteria and fungi.

In one embodiment, the topical composition includes rosehip oil. Rosehip seed oil is high in essential fatty acids and vitamin E which are proven to promote healthy skin. Rosehip seed oil is rich in linoleic and linolenic acids which are important skin nutrients.

In one embodiment, the topical composition includes meadowfoam seed oil, which is a waxy oil, similar to jojoba. Meadowfoam seed oil is rich texture and is able to be used for salves, balms, and ointments, offering substantivity, along with barrier formation, to lock in the skin's natural moisture to help prevent dryness and soften the skin. Meadowfoam Seed Oil is so superior as an anti-oxidant that it may be used to extend the shelf life of other more fragile oils and oil blends.

In one or more embodiments, waxes can be used within 2%-40% by weight of the topical layer. One example wax can be a beeswax.

In one embodiment, the topical composition includes carnauba wax, which is a non-gelling thickener, viscosity and consistency enhancer (provides good texture and stability due to high melting point), and emollient and moisturizer.

In one embodiment, the topical composition includes rice bran wax. The presence of rice bran wax can reduce the incidence of dry and flaky skin when applied.

In other example embodiments, the range of percentages can be different. This list of different formulas and specialized ingredients is not exhaustive and for illustration of different possible uses. Furthermore, the specialized ingredients can be used for other purposes than described. The formulas and ingredients are designed to create a combination of a calming effect on diaper rash and to only activate when the temperature of the wax is raised above the ambient temperature. The ingredients are melted together in the liquid form, applied or stamped into the chassis of the diaper, and then cooled back into a wax or wax-like form once in place.

In an example embodiment, the topical layer can be sent to a diaper manufacturer in drums, such as fifty-five gallon drums. There can be a heat jacket that fits over each drum, warming a solid form of the topical layer from a wax-like state into a liquid state. The topical layer can then be applied to a top woven layer using a straight line machine. In different embodiment, a zebra pattern can be used for application or other pattern type. In one or more embodiments, the pattern used may be used to prevent thickness during melting.

In one embodiment, a diaper manufacturer can apply around five grams of topical layer per diaper and spiral the top woven layer in large quantities.

FIG. 2 illustrates a top view of a diaper 200 with the topical layer 205 applied on an absorbent layer 210 in a rectangular shape according to various embodiments of this disclosure. In one or more embodiments, there is a top sheet between the topical layer 205 and the absorbent layer 210. In various embodiments, the top sheet and topical layer 205 may form a liner that is separate from diaper 200.

Diaper 200 includes a protective area 215. The protective area 215 is defined by the absorbent layer 210 in FIG. 2 is for illustration purposes only and can be a specific area or multiple areas of the absorbent layer 210. The protective area 215 can be determined based on areas of the diaper with the highest possibility of diaper rash for the wearer. For convenience of discussion, the protective area is illustrated as the area of the absorbent layer.

FIG. 3 illustrates a top view of a diaper 300 with the topical layer 305 on an absorbent layer 310 in a rectangular shape with concave sides 315 along the length of the diaper 300 according to one embodiment of the present disclosure. In one or more embodiments, there is a top sheet between the topical layer 305 and the absorbent layer 31. In various embodiments, the top sheet and topical layer 305 may form a liner that is separate from diaper 300.

Figure 4:
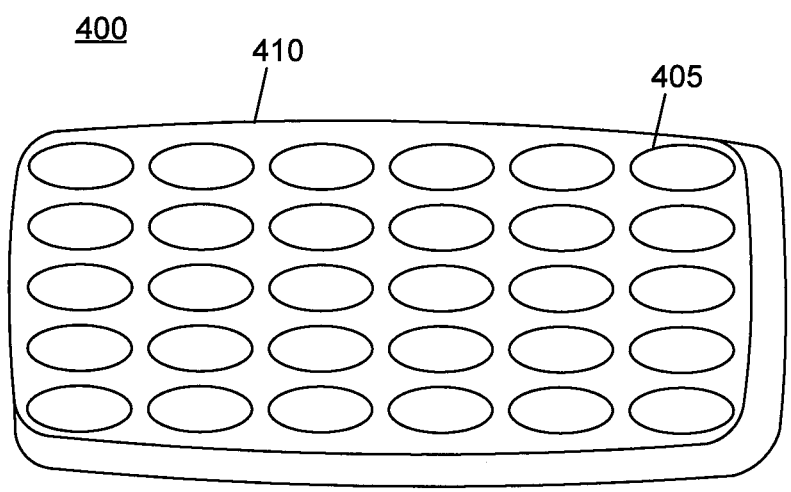
FIG. 4 illustrates an embodiment of the topical layer applied on an absorbent layer of a pad in accordance with disclosed embodiments.

FIG. 4 illustrates a top view of a pad 400 in a rectangular shape with a topical layer 405 on the absorbent layer 410 according to one embodiment of the present disclosure. In one or more embodiments, there is a top sheet between the topical layer 405 and the absorbent layer 410. In various embodiments, the top sheet and topical layer 405 may form a liner that is separate from absorbent layer 410.

Figure 5:
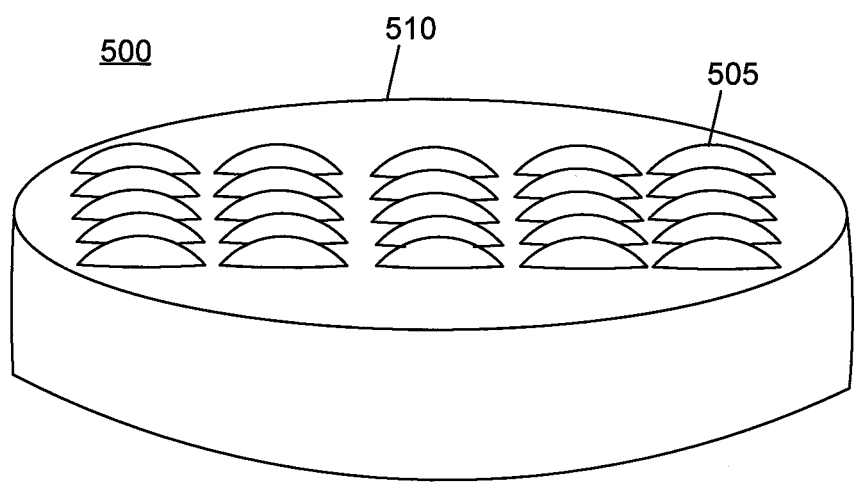
FIG. 5 illustrates an embodiment of the topical layer applied on an absorbent layer of a pad in accordance with disclosed embodiments.

FIG. 5 illustrates a side view of a pad 500 in a cylindrical shape with a topical layer 505 on the absorbent layer 510 according to one embodiment of the present disclosure. In one or more embodiments, there is a top sheet between the topical layer 505 and the absorbent layer 510. In various embodiments, the top sheet and topical layer 505 may form a liner that is separate from absorbent layer 510.

FIGS. 2-5 illustrate different embodiments of the topical layer in accordance with disclosed embodiments. The embodiments shown in FIGS. 2-5 are for illustration only. Other embodiments could be used without departing from the scope of the present disclosure. The topical layers are illustrated as a plurality of domes evenly spaced across the absorbent layers, but any shapes or patterns can be used to pattern the topical layer. For example, the topical layers can be shaped with a flat top surface, as a dome structure, or irregularly. The shapes can be different for each row and/or column. While the pattern in FIG. 4 is illustrated as covering the entire absorbent layer, different patterns can be applied to partial areas of the absorbent layer as illustrated in FIG. 5 with the pattern in a horizontal strip across the pad.

The liners, pads or diapers themselves can comprise different shaped surfaces for optimal use of the topical layer. The liners, diapers or pads include different thickness for holding or concentrating the wax after melting from use. For example, the thickness at the center of the pad can be reduced from the outside edges of the pad.

Figure 6:
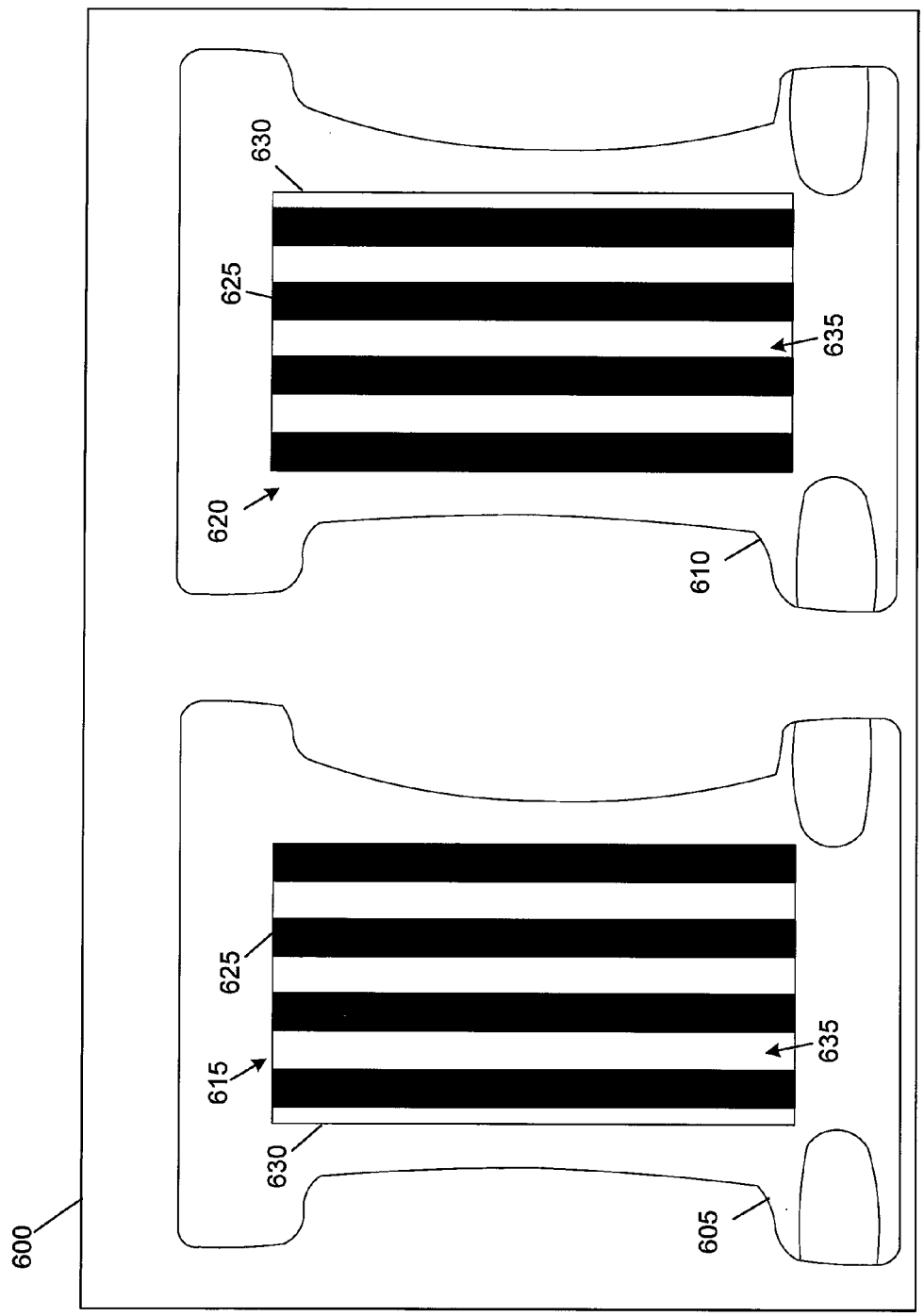
FIG. 6 illustrates a first pattern on a first diaper and a second pattern on a second diaper in a package together in accordance with disclosed embodiments.

FIG. 6 illustrates a first pattern 615 on a first diaper 605 and a second pattern 620 on a second diaper 610 in a package 600 together in accordance with disclosed embodiments. While FIG. 6 illustrates two diapers in a package, any amount of diapers can be included in a package. While FIG. 6 illustrates two diapers in an open position, the diapers may be folded or stored in any manner. Instead of diapers, liners may be used with different patterns in a single package. The diapers or liners may also be packed in any type of packing, such as, but not limited to, a plastic wrap packaging, a cardboard box, a box of recycled material, paper packing, and the like.

In certain embodiments, the topical layer 625 is hydrophobic requiring selective application on a top sheet of the absorbent layer 630. The topical layer 625 being applied in a pattern and not across the entire absorbent layer 630 allows the absorbent layer 630 to absorb any moisture found in the diaper. Because the topical layer 625 is composed of a hydrophobic material, applying the topical layer 625 across the entire absorbent layer 630 could trap the moisture on the skin of the wearer of the diaper.

Along with providing a barrier, the topical layer 625 also provides soothing benefits to the wearer of the diaper and needs to be applied across the entire protective area 635. The protective area 635 can be across the entire surface of the absorbent layer 630 or focused on the highest problem areas for diaper rash.

For maximum effectiveness to the wearer, the entire protective area 615 could be covered over a plurality of diapers. In other words, the topical layer 625 is applied in different patterns on the protective area 635 of each diaper in a pack 600 of diapers in order for the topical layer 625 to affect the entire troubled region on the wearer. In different embodiments, the protective area 615 could cover the entire absorbent layer or could be smaller than the area of the absorbent layer.

FIG. 6 illustrates a pack 600 including a first diaper 605 and a second diaper 610. The first diaper 605 and the second diaper 610 include the same protective areas 635, but have the topical layer 625 applied in a first pattern 615 and a second pattern 620. The first pattern 615 and the second pattern 620 are different in order to allow moisture to pass to the absorbent layer 630, while covering the entire troubled area between using both the first diaper 605 and the second diaper 610 found in together in pack 600. In some embodiments, the entire protective area 615 is covered by using more than two diapers.

In one or more embodiments, the first pattern 630 and second pattern 620 overlap. In other embodiments, the patterns 620 and 630 do not overlap. When using the term overlapping, the patterns do not physically overlap one another, but cover at least some of the same areas of the corresponding diaper for each pattern. For example, if two patterns overlap, both may cover the top portion of the protected area for the corresponding diaper for each pattern.

While both the first pattern 615 and the second pattern 620 illustrated are patterned as stripes along the length of the diapers, the patterns can be applied in any shape or design, such as a matrix of dots. Furthermore, the stripes are illustrated parallel to each other, but also can be patterned perpendicular or at an angle. The patterns can also be non-symmetrical or irregular.

The first pattern 615 can be a different shape or pattern than the second pattern 620. The first pattern 615 and second pattern 620 could both partially cover certain areas of the protective areas 635. For example, the areas that experience the most diaper rash could be covered by both the first pattern and second pattern while areas that experience less diaper rash could be split between the diapers packaged together. When other shapes, such as dots, are used, the patterns are offset in order to cover the entire protective area 635 between the diapers packaged together.

FIG. 6 references diapers packaged together, but other embodiments include liners comprising a topical layer and a top sheet. The liners can be packaged without diapers. The liners of a package can each include a pattern with at least two or more different patterns between the liners.

Figure 7:
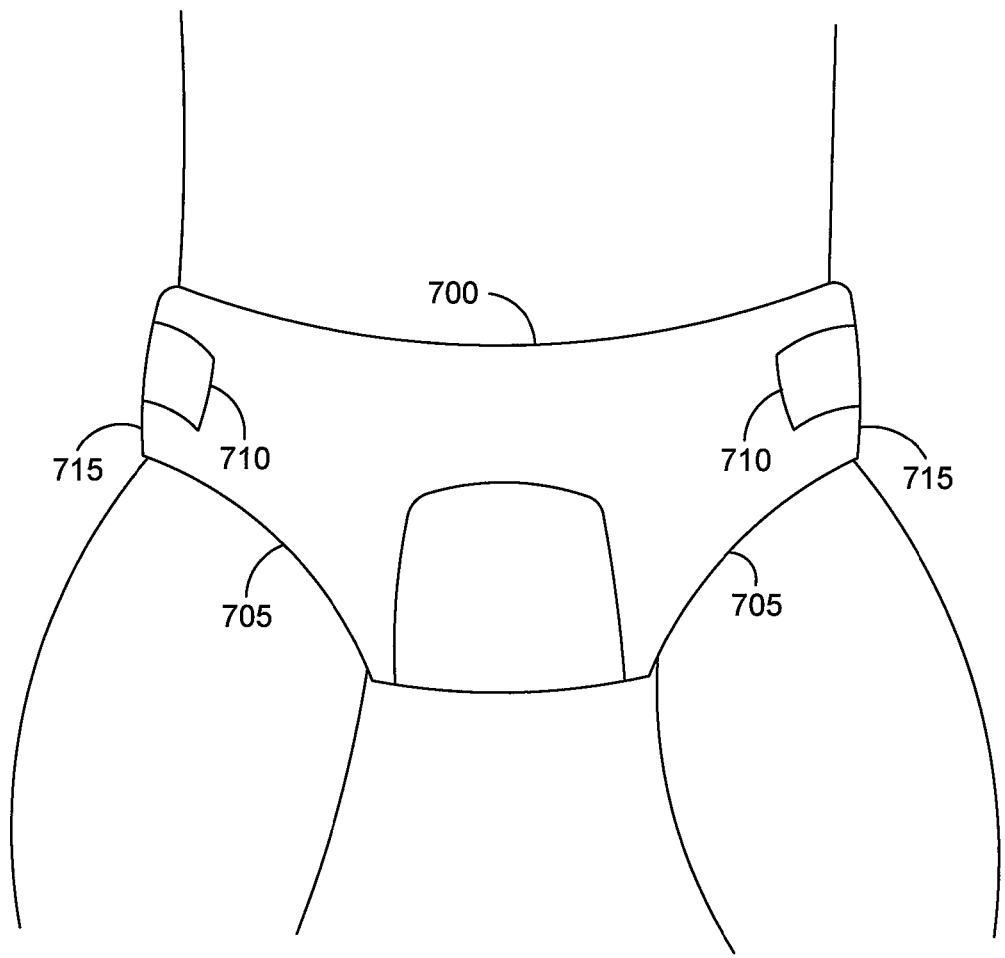
FIG. 7 illustrates a diaper worn on a wearer in accordance with disclosed embodiments.

FIG. 7 illustrates a diaper 700 worn on a wearer according to one embodiment of the present disclosure. The embodiment shown in FIG. 7 is for illustrations only. Other embodiments could be used without departing from the scope of the present disclosure.

For use of the diaper 700, the caregiver removes the enclosing layer exposing the topical layer. The caregiver places the diaper 700 on the baby with the leg linings 705 around the legs of the baby and connects the fasteners 710 to the tabs 715 on the front end of the diaper 700. The topical layer contacts the wearer and, for example, after 2-4 minutes of drying time, the topical layer melts to provide a calming effect on the wearer, for prevention or reduction of diaper rash. The diaper 700 can also include features such as color changing notification for changing, different designs or illustrations, different colors, or any other features found in diapers.

In one embodiment, when the topical layer is within a separate liner, the user can remove the enclosing layer from the liner and place the liner between the user and the diaper.

Figure 8A:
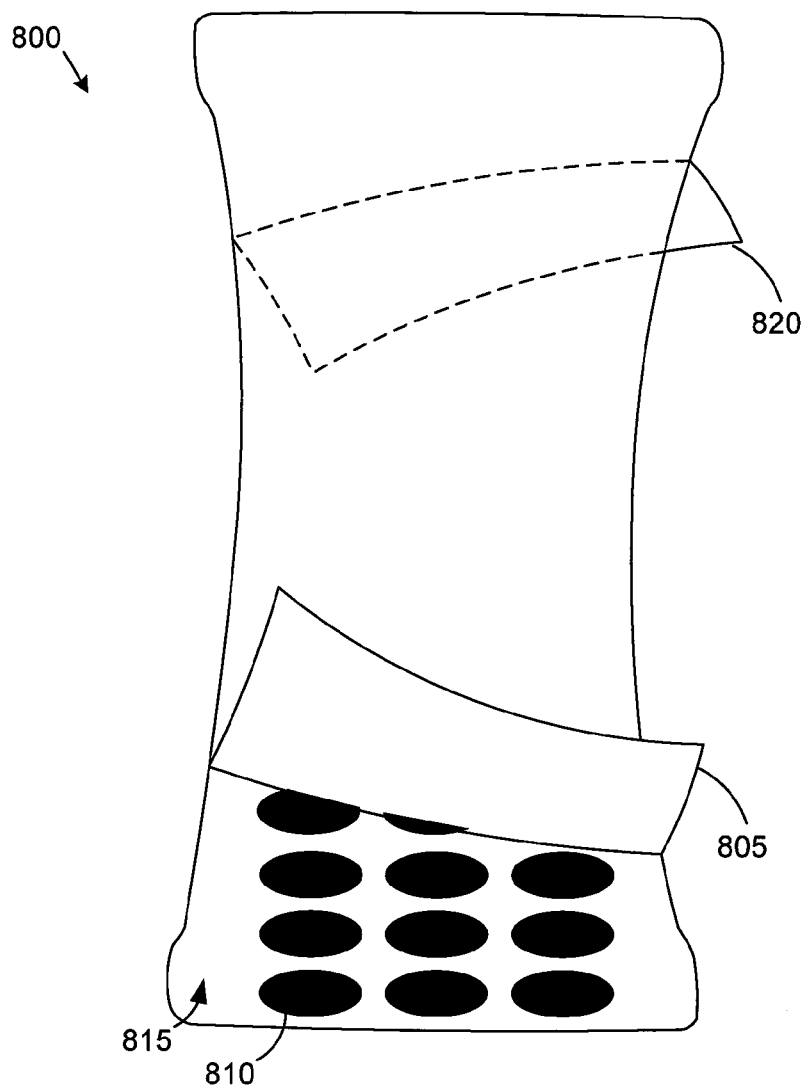
FIGS. 8A and 8B illustrate a liner according to one embodiment of the present disclosure.
Figure 8B:
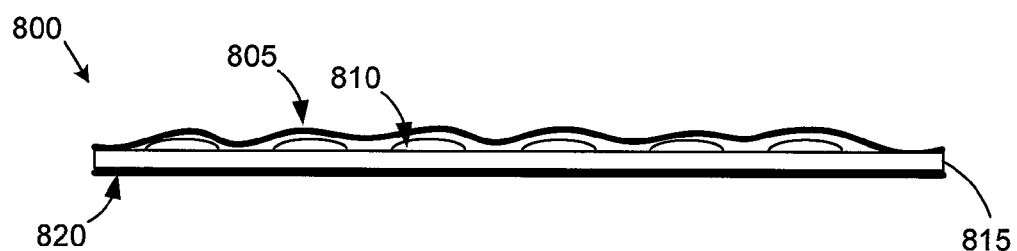

FIGS. 8A and 8B illustrate a liner 800 according to one embodiment of the present disclosure. The embodiments shown in FIGS. 8A and 8B are for illustrations only. Other embodiments could be used without departing from the scope of the present disclosure. Liner 800 can include an enclosing layer 805, a topical layer 810, a top sheet 815, and an enclosing layer 820.

The top sheet 815 can be hydrophilic non-woven material designed to quickly transfer fluids. The non-woven material can be liquid permeable. The top sheet 815 can have a topical layer 810 on a side, the side shown in FIG. 8A. In other embodiments, other sides may include the topical layer 810. In yet other embodiments, the topical layer 810 may permeate the top sheet 815 during application and be on more than one side and within top sheet 815. The top sheet 815 can be comprised of polypropylene, cotton, polyethylene, a combination, and the like.

In one example embodiments, topical layer 810 can include a hydrophobic mixture (or composition) that includes a topical composition and a solidifying agent. In one example, the topical composition is mixed with the solidifying agent. In another example, the solidifying agent encapsulates the topical composition. The topical layer 810 can include portions of a hydrophobic mixture in a pattern onto top sheet 815. The pattern can include patterns as shown in FIGS. 2-6. The pattern can allow for liquid to permeate between the portions of hydrophobic mixture applied to the top sheet 815.

In one example embodiment, enclosing layers 805 and 820 can be used to prevent the topical layer 810 from being removed from the top sheet 815. The enclosing layers 805 and 820 can be comprised of an impermeable material, such as wax or parchment paper. In one embodiment, another layer of adhesive can be included between enclosing layer 820 and top sheet 815. In yet a further example, an absorbent layer can be included between enclosing layer 820 and top sheet 815, or between the adhesive layer and top sheet 815.

Figure 9A:
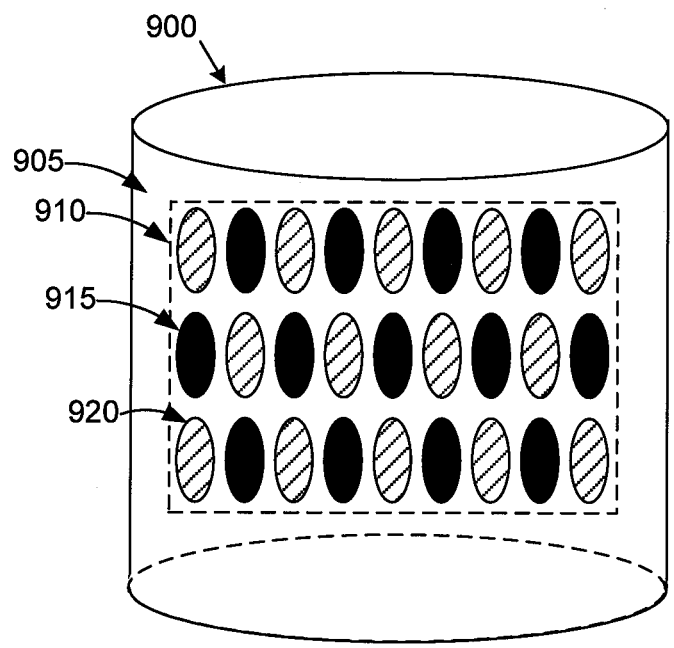
FIGS. 9A and 9B illustrate a spool according to one embodiment of the present disclosure.
Figure 9B:
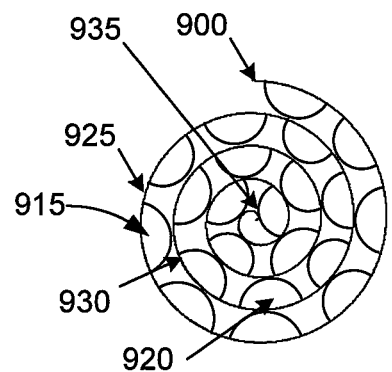

FIGS. 9A and 9B illustrate a spool 900 according to one embodiment of the present disclosure. The embodiments shown in FIGS. 9A and 9B are for illustrations only. Other embodiments could be used without departing from the scope of the present disclosure. Spool 900 can include a top sheet 905, a cutout view 910 of the inside of two spool 900 layers 925-930, a first pattern 915 of topical composition on one spool 900 layer 925, and first pattern 920 of topical composition on a second spool 900 layer 930. The layers 925-930 of spool 900 wrap around each other to form a spiral. Each layer of the spiral from the center 935 of the spiral represents a different layer.

One or more embodiments of this disclosure provide applying a topical layer to a top sheet, in a continuous process. In this process, patterns of topical composition are placed on a top sheet and spooled onto a large roll, referred to herein as a spool, for later use in the manufacture of the liners or diapers.

In one example embodiment, the topical composition is not applied to the entire surface of the top sheet, but a pattern resulting in approximately 30% coverage is desired. Spots of topical composition increase the overall thickness of the top sheet. One or more embodiments of this disclosure recognize and take into account that as the pattern is spooled onto the top sheet, these spots 915-920 can overlap and cause the overall spool diameter to increase beyond the diameter of the top sheet alone. The topical layers shown on spool 900 are not to scale.

Figure 10:
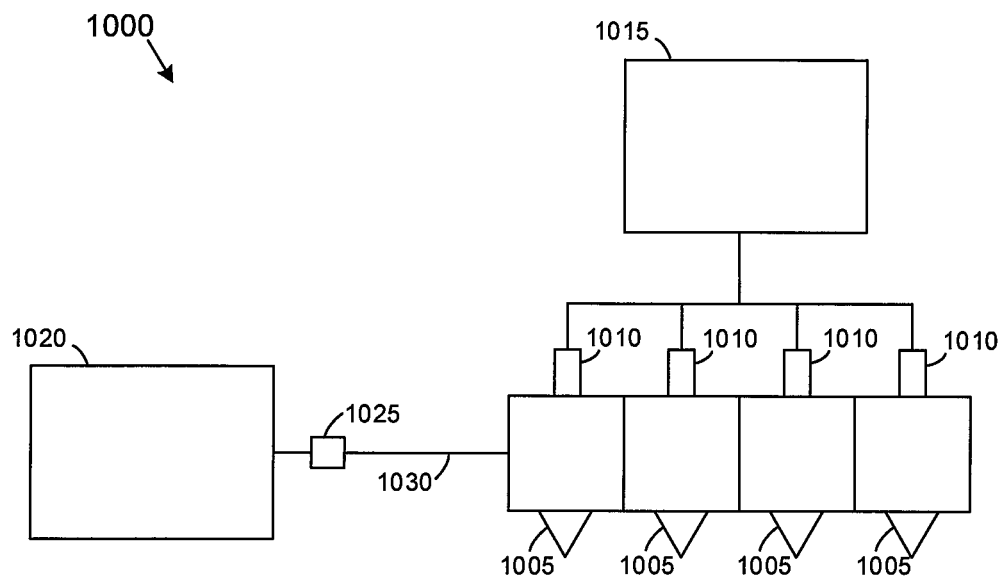
FIG. 10 illustrates a manufacturing assembly for producing a package of diapers in accordance with disclosed embodiments.

FIG. 10 illustrates a manufacturing assembly 1000 for producing a package of diapers or liners in accordance with disclosed embodiments. The embodiment shown in FIG. 10 is for illustrations only. Other embodiments could be used without departing from the scope of the present disclosure.

The manufacturing assembly 1000 includes a plurality of extrusion heads 105, a plurality of solenoid valves 1010, a programmable logic controller (PLC) 1015, a heated tank 1020, a pump 1025, and a heated hose 1030. The heated tank 1020 stores and heats the topical wax. The topical wax is heated in the heated tank 1020 to a liquid state for transfer through the heated hose 1030 and the plurality of extrusion heads 1005 to the diaper. A pump 1025 pumps the liquid wax through the heated hose 1030 to the plurality of extrusion heads 1005. The pump 1025 can be hydraulic or pneumatic. The plurality of extrusion heads 1005 controls the flow of the liquid wax onto the diaper. Each of the extrusion heads 1005 can be controlled separately by a solenoid valve 1010. The plurality of solenoid valves 1010 control the plurality of extrusion heads 1005 in a manner that the liquid wax can be applied in different patterns and amounts. A PLC 1015 controls the plurality of solenoid valves 1010. The PLC 1015 is programmed to operate the plurality of solenoid valves 1010 to apply the pattern on each diaper. The PLC 1015 applies the topical wax in a manner that over the use of a pack of diapers or liners the entire affected area is covered.

Figure 11A:
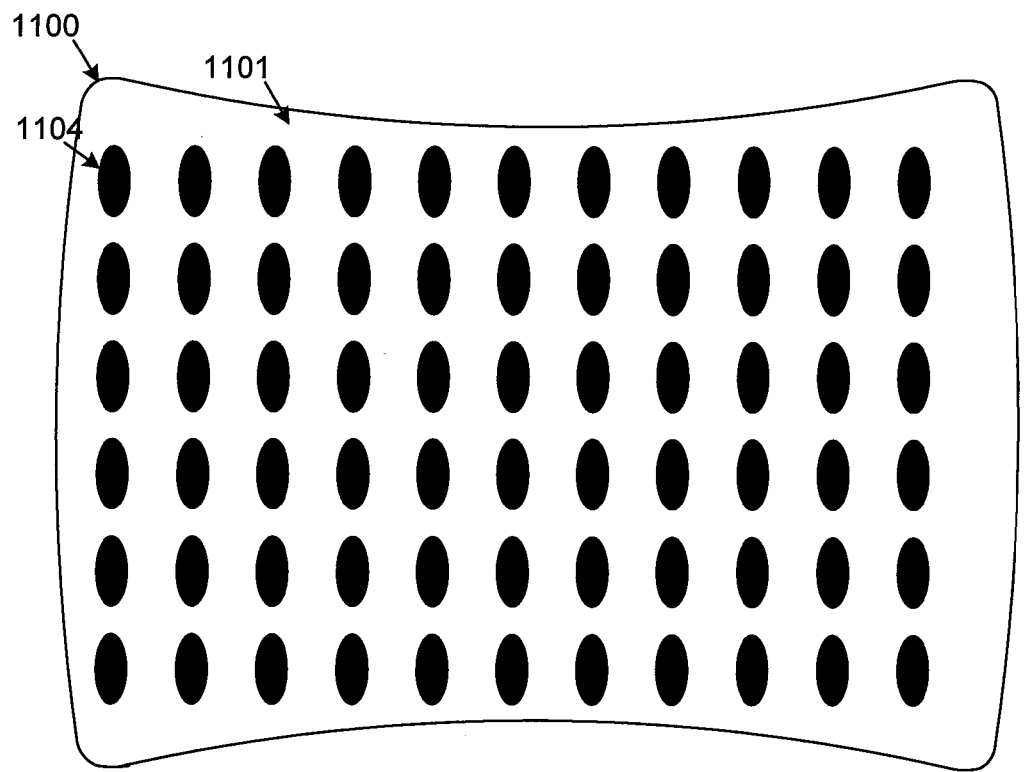
FIGS. 11A and 11B illustrate a top view of a liner and liner according to one embodiment of the present disclosure.
Figure 11B:
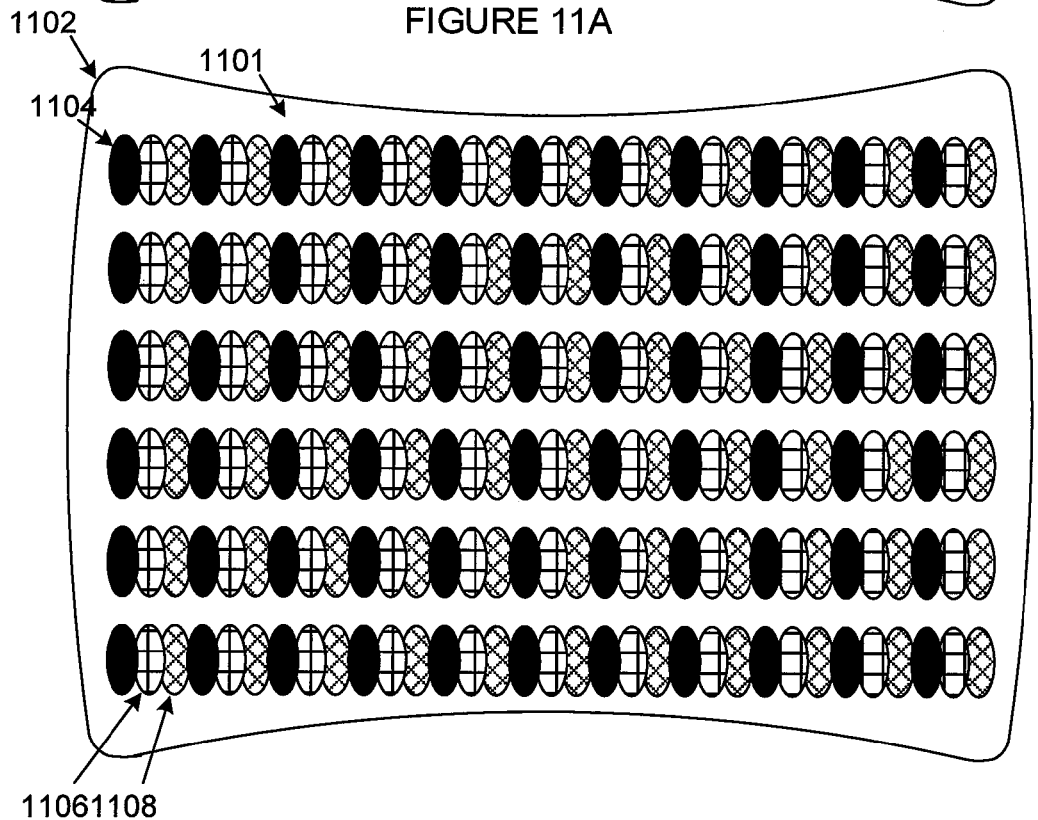

FIGS. 11A and 11B illustrate a top view of a liner 1100 and liner 1102 according to one embodiment of the present disclosure. In one or more embodiments, there is a top sheet 1101 with a topical layer 1104. Liner 1100 shows a single topical layer 1104, while liner 1102 shows the topical layer 1104 with additional layers 1106-1108 superimposed on liner 1102 to show where each would be positioned on respective top sheets 1101.

One or more embodiments of this disclosure provide packing as many linear feet of the product-applied top sheet on each roll. Rectilinear patterns of topical composition tend to stack on top of each other, leaving large areas of top sheet spaced apart from the layer beneath. Rectilinear patterns, such as shown in FIGS. 11A and 11B pack all of the application spots in "columns" on the spool, leaving large areas where the fabric has no stacking spots. One example embodiment of this disclosure uses rectilinear patterns. An additional problem with the rectilinear pattern is that it spools in aligned columns of product that can result in roll instability. That is, the roll will have a tendency to slide sideways on the spool. Better packing and stability of the application spots is achieved by seeking out patterns that fill in the areas of unused fabric for maximum packing and maximum linear feet per roll.

Figures 12A, 12B:
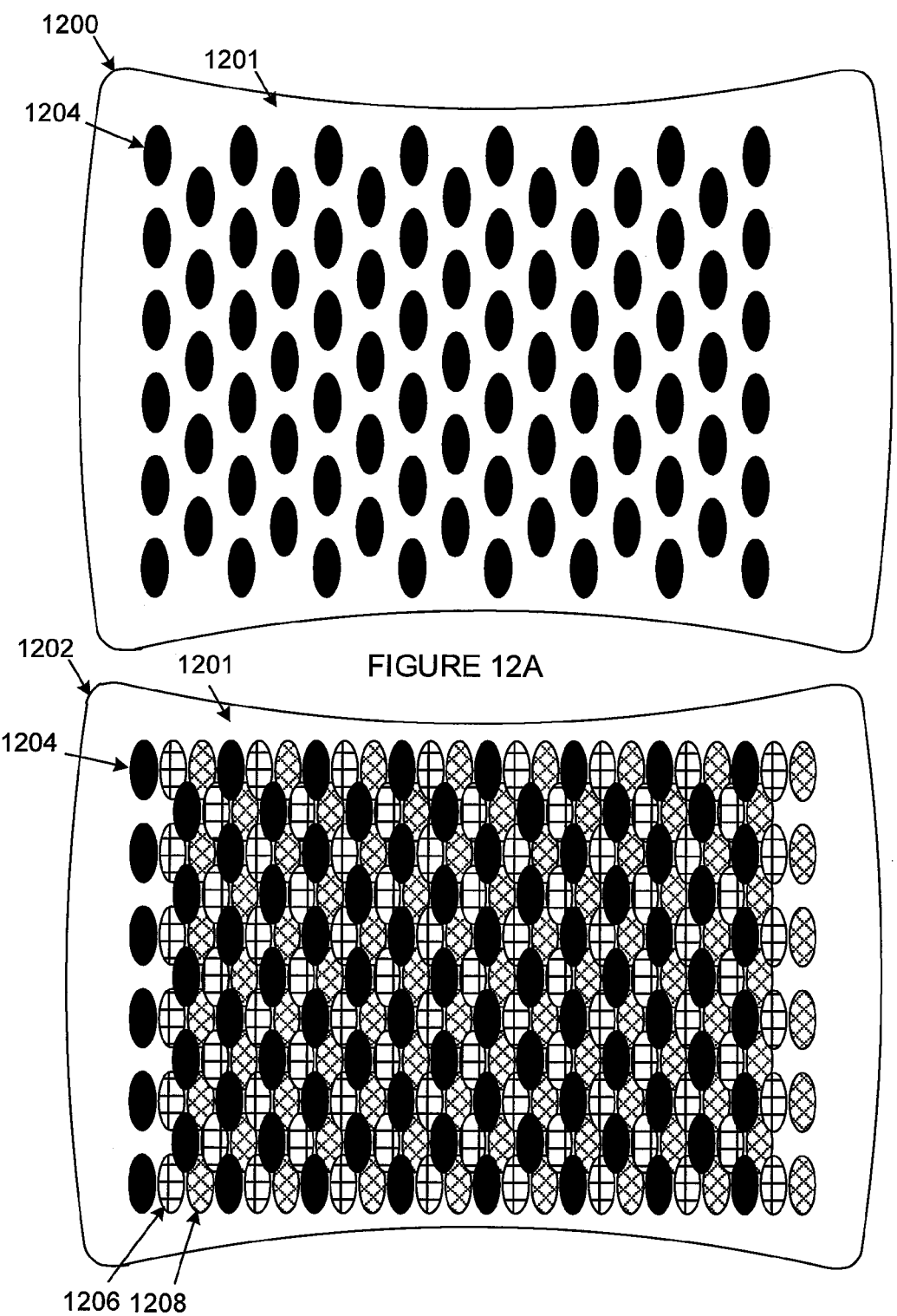
FIGS. 12A and 12B illustrate a top view of a liner and liner with an offset pattern according to one embodiment of the present disclosure.

FIGS. 12A and 12B illustrate a top view of a liner 1200 and liner 1202 with an offset pattern according to one embodiment of the present disclosure. In one or more embodiments, there is a top sheet 1201 with a topical layer 1204. Liner 1200 shows a single topical layer 1204, while liner 1202 shows the topical layer 1204 with additional layers 1206-1208 superimposed on liner 1202 to show where each would be positioned on multiple respective top sheets 1201. In this embodiment, the pattern constitutes a simple offset of every second row of spots to a location midway between the previous row. This pattern improves the packing, reducing overlapping of the spots as the top sheet spools onto the roll.

Figure 13A:
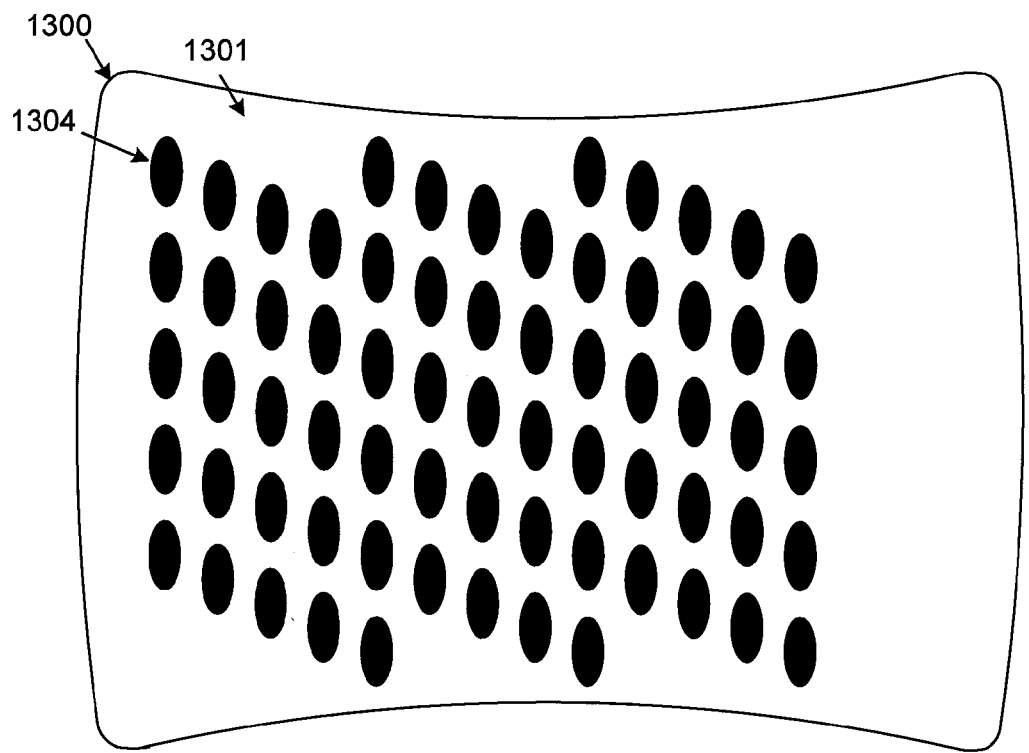
FIGS. 13A and 13B illustrate a top view of a liner and liner with an offset pattern according to one embodiment of the present disclosure.
Figure 13B:
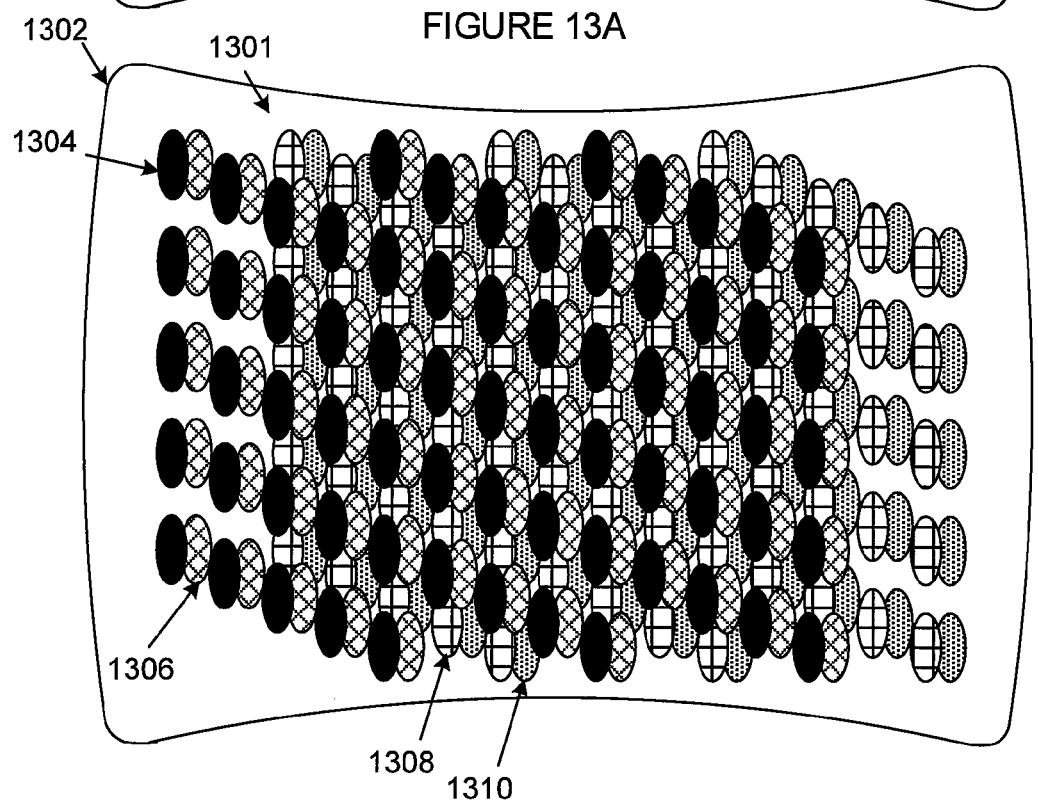

FIGS. 13A and 13B illustrate a top view of a liner 1300 and liner 1302 with an offset pattern according to one embodiment of the present disclosure. In one or more embodiments, there is a top sheet 1301 with a topical layer 1304. Liner 1300 shows a single topical layer 1304, while liner 1302 shows the topical layer 1304 with additional layers 1306-1310 superimposed on liner 1302 to show where each would be positioned on multiple respective top sheets 1301. In this embodiment, the pattern offsets each row by a fifth of the spot pitch from the prior row, creating even greater packing of the spots and minimizing the statistical probability that one spot will wrap onto a prior spot.

One can see that this pattern is a repeating set of five rows. In actual application, the pattern could be repeating every "n" rows, where "n" is any integer greater than 1. Furthermore, maximum packing can also be achieved where each row is offset by "a/n" from the prior row, where "a<n" and is a random offset from the prior row, having a different value for each row, resulting in a disorderly pattern.

Furthermore, this same principle can apply to the rows of spots, where the spots do not need to be applied in straight rows. The spots could be applied in a random or pseudo-random pattern on the fabric to accomplish the required function of maximizing the statistical probability that spots will not overlap as they are spooled onto the roll.

One example embodiment of this disclosure provides a fabric sheet, or top sheet, for treating diaper rash. The fabric sheet includes a topical composition applied to a porous fabric such that the application spots of the product are applied in a non-rectilinear pattern. In one example, the fabric sheets are pre-assembled to a diaper. In another example, the sheets are packaged for use within a diaper as a separate product. In yet another example, the sheets are packaged for use directly on an infant apart from a diaper. In yet another example, the topical composition is applied to the fabric to provide approximately 30% coverage of the fabric area. In yet another example, the fabric sheets are pre-assembled to a diaper. In yet another example, the topical composition is applied to the fabric in a regular pattern of offset rows of spot applications. In yet another example, the fabric sheets are pre-assembled to a diaper. In yet another example, the diaper rash product is applied to the fabric in a random pattern of spot applications. In yet another example, the fabric sheets are pre-assembled to a diaper As used herein, there are many references to a topical composition. Any such reference could also include the topical composition mixed with a solidifying agent or encapsulated by a solidifying agent.

Figure 14:
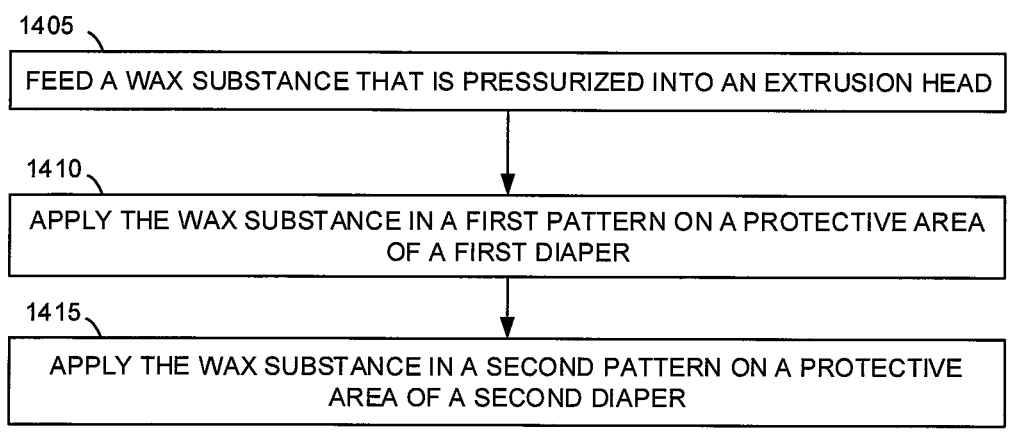
FIG. 14 illustrates a process for manufacturing a group of diapers in accordance with disclosed embodiments.

FIG. 14 illustrates a process for manufacturing a group of diapers or liners in accordance with disclosed embodiments. The different operations of the process can be controlled by a processor executing instructions on a memory element.

In operation 1405, the manufacturing system feeds a wax substance that is pressurized for use as a topical layer over a protective area for each of a plurality of diapers. The protective area is positioned on each of the plurality of diapers in a manner for consistent application on a wearer. In some embodiments, the protective area is fully within the area of the absorbent layer. The wax substance is pressurized by a hydraulic pump and applied in the different patterns, such as alternating patterns, through a plurality of extrusion heads In operation 1410, the manufacturing system applies the wax substance in a first pattern on a protective area of a first diaper. The manufacturing system controls each of the plurality of extrusion heads using solenoid valves. The timing of the solenoid valves is controlled using a programming logic control (PLC) that is programmed to ensure every portion of the protective area is covered by either the first pattern on the first diaper or the second pattern on the second diaper.

In operation 1415, the manufacturing system applies the wax substance in a second pattern on a protective area of a second diaper. The portions of the protective area of the first diaper not covered by the first pattern are covered by the second pattern on the protective area of the second diaper.

The process as described in FIG. 14 can be used to applying alternating patterns to a top sheet. This can include, for example, two or more patterns, five patterns, or many more patterns as desired. These patterns can all be different, or similar and offset, and/or alternating.

Although the present disclosure has been described with exemplary embodiments, various changes and modifications may be suggested to one skilled in the art. It is intended that the present disclosure encompass such changes and modifications as fall within the scope of the appended claims.

What is claimed is:

1. A medical dressing, comprising:
   a first layer comprising a non-woven material capable of being liquid permeable;
   a second layer comprising a topical composition and a solidifying agent, wherein the second layer is positioned on a side of the first layer, wherein the first layer is configured to prevent thickness of the topical composition when melted; and
   a removable third layer comprising a material capable of being liquid impermeable, wherein the third layer is positioned on the second layer opposite the first layer.

2. The medical dressing of claim 1, wherein the second layer comprises a pattern.

3. The medical dressing of claim 2, wherein the pattern covers only a portion of the at least one side of the first layer.

4. The medical dressing of claim 1, further comprising:
   a fourth layer comprising the material capable of being liquid impermeable, wherein the fourth layer is positioned on the first layer opposite the second layer.

5. The medical dressing of claim 4, further comprising:
   a fifth layer comprising an adhesive, wherein the adhesive is positioned between the fourth layer and the first layer.

6. The medical dressing of claim 1, wherein the topical composition is mixed with the solidifying agent.

7. The medical dressing of claim 1, wherein the solidifying agent encapsulates the topical composition.

8. A medical dressing for treating diaper rash, comprising:
   a top sheet comprising a non-woven material capable of being liquid permeable; and
   a topical layer comprising 20-30% by weight of organic shea butter and 20-30% by weight of pure white beeswax, and a plurality of specialized components, wherein the topical layer is positioned on a side of the top sheet wherein the topical layer is a wax substance adapted to melt when the medical dressing is used, and wherein the topical layer is applied to the absorbent layer in a pattern that includes a number of individual portions of the topical layer positioned on the absorbent layer, and wherein the first layer is configured to prevent thickness of the wax when the wax is melted.

9. The medical dressing of claim 8, wherein the topical layer comprises 25% by weight of the organic shea butter and 25% by weight of the pure white beeswax.

10. The medical dressing of claim 8, wherein the topical layer is positioned within the top sheet and on an opposite side of the side of the top sheet.

11. The medical dressing of claim 8, further comprising:
    an enclosing layer comprising an impermeable material enclosing the topical layer between the top sheet and the enclosing layer.

12. The medical dressing of claim 8, wherein the plurality of specialized components comprise zinc oxide power, liquid lanolin, organic dandelion root powder and chickweed herb powder.

13. The medical dressing of claim 8, wherein the plurality of specialized components comprise zinc oxide powder, liquid lanolin, organic aloe vera powder, and chamomile flowers.

14. The medical dressing of claim 8, wherein the plurality of specialized components comprise zinc oxide power, liquid lanolin, cod liver oil, and chamomile flowers powder.

15. The medical dressing of claim 8, wherein the plurality of specialized components comprise zinc oxide powder, cod liver oil, chickweed herb powder, liquid lanolin, and dandelion root powder.

16. The medical dressing of claim 8, wherein the plurality of specialized components comprise 2% by weight of chickweed herb powder, 2% by weight of dandelion root powder, 40% by weight of zinc oxide powder, 4% by weight of cod liver oil, and 2% by weight of liquid lanolin.

17. The medical dressing of claim 8, wherein the plurality of specialized components comprise chickweed herb powder, dandelion root powder, zinc oxide powder, cod liver oil, chamomile oil, and phenonip.

\* \* \* \* \*